United States Patent [19]

Mackman

[11] Patent Number: 4,923,398
[45] Date of Patent: May 8, 1990

[54] FACE PLATE FOR DENTAL ARTICULATOR

[76] Inventor: Jay L. Mackman, 2105 W. Applewood La., Glendale, Wis. 53209

[21] Appl. No.: 108,057

[22] Filed: Oct. 13, 1987

[51] Int. Cl.$^5$ ............................................. A61C 11/00
[52] U.S. Cl. ......................................... 433/60; 433/65
[58] Field of Search ..................................... 433/60, 65

[56] References Cited

U.S. PATENT DOCUMENTS

| | | | |
|---|---|---|---|
| 1,814,750 | 7/1931 | Fritzenwallner | 433/60 |
| 2,765,533 | 10/1956 | McMorris | 433/60 |
| 3,423,834 | 2/1969 | Irish | 433/54 |
| 3,844,040 | 10/1974 | Willis | 433/60 |
| 4,096,632 | 6/1978 | Perry | 433/60 |
| 4,242,087 | 9/1978 | Lee | 433/54 |
| 4,358,269 | 11/1982 | Hay et al. | 433/60 |
| 4,371,338 | 2/1983 | Mercer et al. | 433/60 |
| 4,412,822 | 7/1983 | Blechner | 433/57 |
| 4,417,873 | 12/1983 | Kulas | 433/60 |
| 4,687,442 | 8/1987 | Wong | 433/60 |
| 4,744,751 | 5/1988 | Finkelstein et al. | 433/60 |

FOREIGN PATENT DOCUMENTS

| | | | |
|---|---|---|---|
| 554148 | 1/1957 | Italy | 433/60 |
| 608919 | 9/1960 | Italy | 433/60 |

Primary Examiner—John J. Wilson
Attorney, Agent, or Firm—Andrus, Sceales, Starke & Sawall

[57] ABSTRACT

A face place assembly unit is provided for fixing a dental cast to one or both of the frame members of a dental articulator. The face plate is multidirectionally positionable relative to the frame member of the articulator, to provide for accurate positioning of a dental cast mounted to one of the frame members relative to a dental cast mounted the other of the frame members. In one embodiment, the face plate unit is provided with a position fixing assembly which allows the dental cast to be accurately positioned relative to a frame member of a dental articulator and then fixed in such relative position. The assembly can then be removed from the articulator and reconnected thereto while maintaining the position of the dental cast relative to the frame member of the articulator to which it was mounted.

12 Claims, 3 Drawing Sheets

FACE PLATE FOR DENTAL ARTICULATOR

BACKGROUND AND SUMMARY

This invention relates to a dental articular, and more particularly to an apparatus for mounting a dental cast onto a dental articulator.

A dental articulator is an apparatus which simulates the movement of a human jaw, and generally includes an upper frame member and a lower frame member. The upper and lower frame members are adapted to have dental casts of a patient's upper and lower teeth, respectively, mounted thereto. The dental casts are formed from impressions of the patient's teeth, to provide an accurate reproduction thereof. With casts of a patient's teeth mounted in this manner on the articulator, a dentist has available an accurate model of a patient's actual dental structure and movement thereof. This allows the dentist to work on the casts of the patient's teeth when performing dental repairs such as bridge work, crowns, splints and dentures, as opposed to working on the actual teeth of the patient.

When mounting the dental casts to the articulator, it is important that the casts be mounted in such a manner as to closely replicate the actual dental structure of the patient. That is, the casts must be accurately located so that the upper and lower casts of the teeth interact in a manner which duplicates the actual interaction of the patient's teeth as closely as possible. This calls for accurate positioning of the casts relative to one another.

It is known to mount the dental casts to the articulator frame members by means of a mounting plate which is removably connectable to the frame members. The mounting plate is generally a flat disc-like member having a threaded hole to receive the threaded portion of a mounting screw which extends through the frame member. The dental cast is secured to the mounting plate using a plaster-like substance, such as plaster of Paris. This form of mounting is generally shown in U.S. Pat. No. 4,417,873 to Kulas.

Plaster mounting of a dental cast to an articulator frame member is a time consuming and messy process. The dental cast must be manually held in position while the wet plaster is placed between the dental cast and the mounting plate. The cast must then be manually held in place while the plaster sets, which can take up to 20 minutes. This step must be performed for mounting both the upper and lower dental casts to the upper and lower frame members of the articulator. Once the plaster has set, the assembly can be removed from the articulator by removing the mounting screw from the threaded opening in the mounting plate. The casts can then be put aside while other work is performed on the articulator, such as mounting another set of casts to the articulator frame members or working on a previously mounted set of dental casts which have been reconnected to the articulator frame members.

The present invention has been developed to overcome problems with the above-referenced procedure for mounting a dental cast to an articulator. The invention allows the dental cast to be mounted to an articulator frame member without the use of a plaster-like material. Additionally, the invention allows the cast to be removed from the frame member of the articulator and put aside, and thereafter be reconnected to the frame member for resumption of work on the dental cast.

In accordance with the invention, a face plate for a dental articulator having opposed spaced frame members includes a body portion adapted to receive a dental cast. The body portion is connectable to one of the frame members of the dental articulator, such as by means of the aforementioned mounting screw, for connecting the dental cast thereto. The body portion has a mounting means associated therewith for physically mounting the dental cast to the body portion. The invention further includes multidirectional positioning means associated with the face plate for providing selective multidirectional positioning of the dental cast relative to the frame member after the cast has been mounted to the articulator frame member. This allows accurate positioning of a dental cast relative to another dental cast mounted to the other of the frame members.

In one embodiment, the invention provides a removable face plate assembly for mounting a dental cast to a frame member of an articulator. The removable assembly can be removed from the frame member and reconnected thereto, while maintaining the position of the dental cast relative to the frame member during such reconnection. The face plate assembly includes a body portion adapted to receive a dental cast. The body portion is connectable to one of the frame members of the articulator for mounting the dental cast thereto. A mounting means is associated with the body portion for mounting the dental cast to the body portion. Positioning means is associated with the face plate assembly for providing selective positioning of the dental cast relative to the frame member after the cast has been mounted to the articulator frame member. This arrangement allows accurate positioning of the dental cast relative to another dental cast mounted to the other frame member of the articulator. The assembly further includes connection means for removably connecting the face plate assembly to the frame member.

The invention thus provides an apparatus which allows multidirectional positioning of a dental cast after it has been mounted to the articulator frame member. After mounting, the position of the cast may be adjusted in an up-down direction relative to the upper and lower frame members, and also in a plane parallel to a transverse plane extending through the frame member.

BRIEF DESCRIPTION OF THE DRAWINGS

The drawings illustrate the best mode presently contemplated of carrying out the invention.

In the drawings.

DETAILED DESCRIPTION OF THE PREFERRED EMBODIMENT

Figure 1:
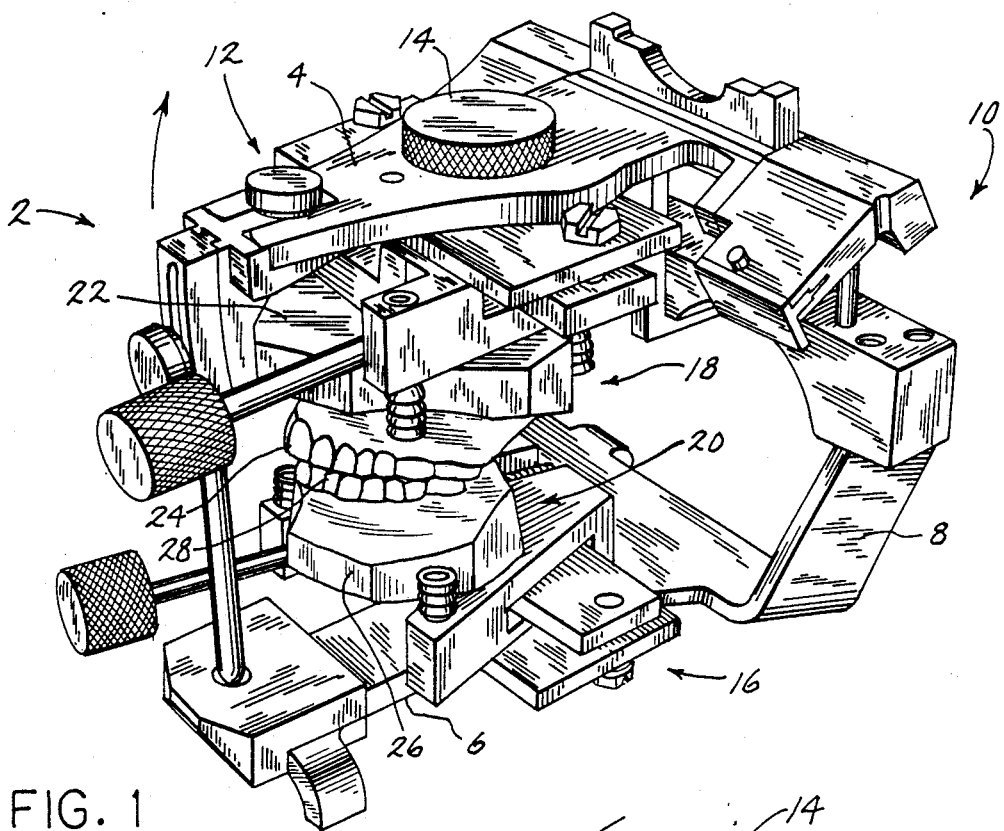
FIG. 1 is an isometric view of a dental articulator incorporating a removable face plate assembly constructed according to the present invention.

As shown in FIG. 1, a dental articulator 2 includes an upper frame member 4 and a lower frame member 6. Lower frame member 6 has a pair of opposed, spaced upstanding members, one of which is shown at 8. A hinge mechanism 10 is provided between upper frame member 4 and the upper ends of the spaced upstanding members extending from lower frame member 6, which simulates the action of a human jaw.

An upper face plate assembly 12 is connected to upper frame member 4 by means of a mounting screw 14, and a lower face plate assembly 16 is connected to lower frame member 6 by means of a mounting screw (not shown) similar to mounting screw 14. Upper face plate assembly 12 is adapted to mount an upper dental cast 18 to upper frame member 4, and lower face plate assembly 16 is adapted to mount a lower dental cast 20 to lower frame member 6. Upper dental cast 18 includes a base portion 22 and a portion 24 which replicates the upper set of teeth of a dental patient. Likewise, lower dental cast 20 includes a base portion 26 and a portion 28 which replicates the lower set of teeth of a dental patient.

Upper face plate assembly 12 and lower face plate assembly 16, with upper dental cast 18 and lower dental cast 20 mounted thereto, respectively, are removable as a unit from the frame members of articulator 2 to which they are mounted. That is, after the dental casts have been mounted to the face plate assemblies and their position relative to one another has been fixed, the face plate assemblies, including the dental casts, can be removed from articulator 2 and put aside while a different set of casts are connected to articulator 2.

Figure 2:
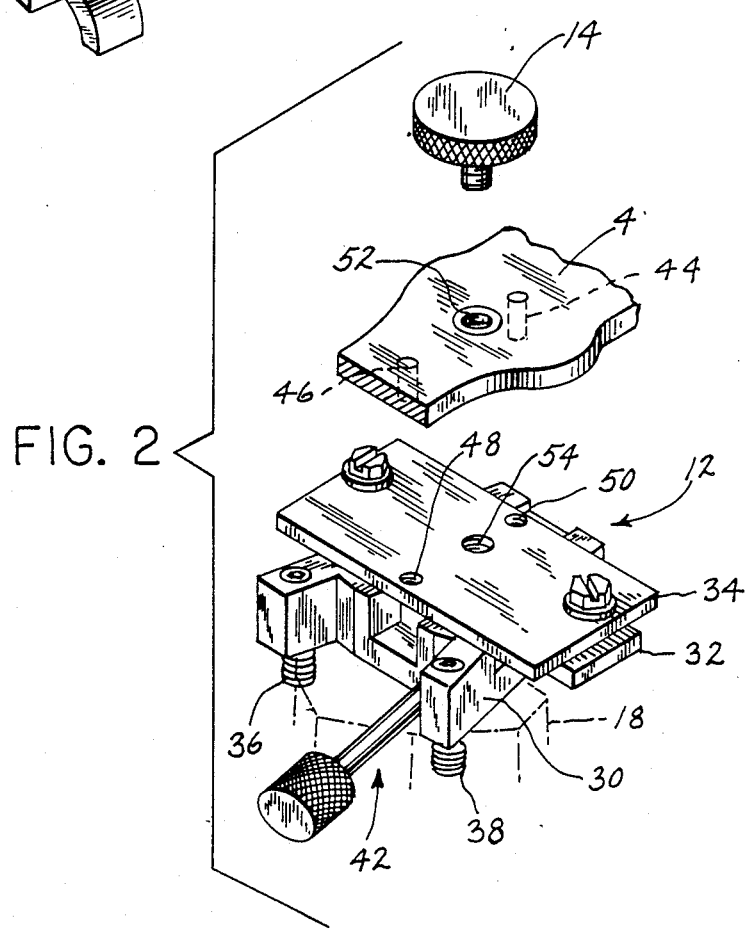
FIG. 2 is an exploded view showing the removable face plate assembly of FIG. 1 and the manner in which it is connected to a frame member of the articulator.

With reference to FIG. 2, upper face plate assembly 12 includes a body portion 30, connectable to frame member 4 by means of a connector plate 32 in combination with a clamping plate 34, as will be explained. Body portion 30 has a pair of stationary finned posts 36, 38 mounted thereto. Finned posts 36, 38, in combination with a finned post 40 which is movable toward and away from finned posts 36, 38 responsive to turning of adjusting screw 42, act to securely mount upper dental cast 18 to upper face plate assembly 12, as will be explained.

As a means for ensuring that upper face plate assembly 12 is consistently located relative to upper frame member 4 when upper face plate assembly 12 is reconnected to upper frame member 4 after having been removed therefrom, upper frame member 4 has a pair of depending locator pins 44, 46 and clamping plate 34 of upper face plate assembly 12 has a pair of locator holes 48, 50 adapted to mate with locator pins 44, 46. A threaded hole 52 is provided in upper frame member 4 between locator pins 44, 46 to receive the threaded portion of mounting screw 14, and clamping plate 34 likewise has a threaded hole 54 between locator holes 48, 50 for receiving the threaded portion of mounting screw 14. Threaded hole 52 in upper frame member 4 is offset from the midpoint of locator pins 44, 46, and likewise threaded hole 54 in clamping plate 34 is offset a like distance from the midpoint of locator holes 48 and 50. With this arrangement locator pins 44, 46 mate with locator holes 48, 50 to ensure proper direction and alignment of upper face plate assembly 12 whenever upper face plate assembly 12 is reconnected to upper frame member 4. Similarly, lower face plate assembly 16 and lower frame member 6 have an identical locator arrangement which ensures proper direction and alignment of lower face plate assembly 16 whenever it is reconnected to lower frame member 6.

Figure 3:
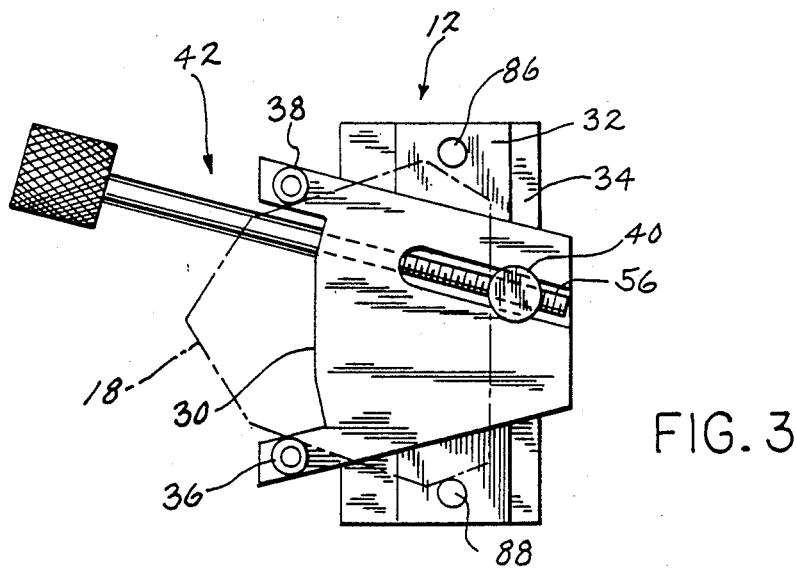
FIG. 3 is a bottom plan view of the removable face plate assembly of FIG. 1.
Figure 6:
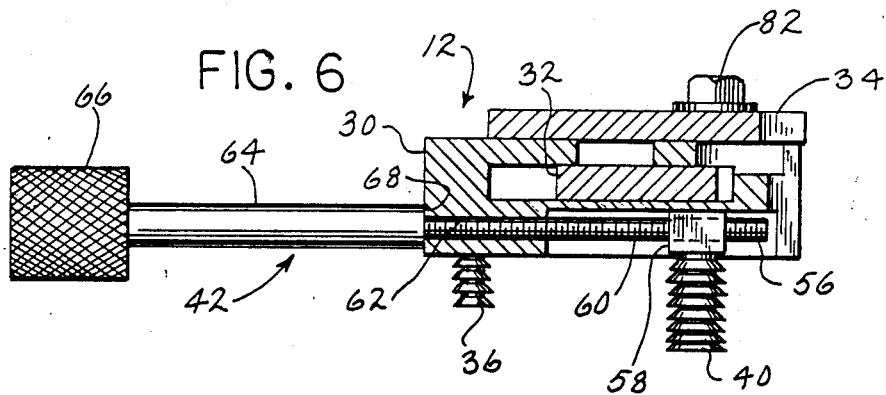
FIG. 6 is a section view taken generally along line 6—6 of FIG. 4.

With reference to FIG. 3, body portion 30 of upper face plate assembly 12 is provided with a pair of spaced stationary finned posts 36, 38, as previously noted. Movable finned post 40 is movable toward and away from stationary posts 36, 38 in response to turning of adjusting screw 42, to securely mount dental cast 18 to body portion 30. Referring to FIGS. 3 and 6, a slot 56 is provided in body portion 30. A base portion 58 of movable finned post 40 is adapted to fit within slot 56 and is movable along the length of slot 56. Base portion 58 of finned post 40 is provided with a threaded opening therethrough, to receive threaded portion 60 of tightening screw 42 extending within slot 56. As best seen in FIG. 6, a threaded passage 62 extends through body portion 30 and opens into slot 56. Threaded passage 62 receives threaded portion 60 of adjusting screw 42. Adjusting screw 42 has a shank 64 with a knurled knob 66 at one end and a shoulder 68 at the other end, from which threaded portion 60 extends. Shoulder 68 is adapted to abut the face of body portion 30 adjacent threaded opening 62, so that turning of adjusting screw 42 provides movement of movable post 40 within slot 56. In this manner, when a dental cast is placed between stationary posts 36, 38 and movable post 40, adjusting screw 42 is turned to draw movable post 40 toward stationary posts 36, 38 to tightly clamp or mount a dental cast to body portion 30.

Figure 7:
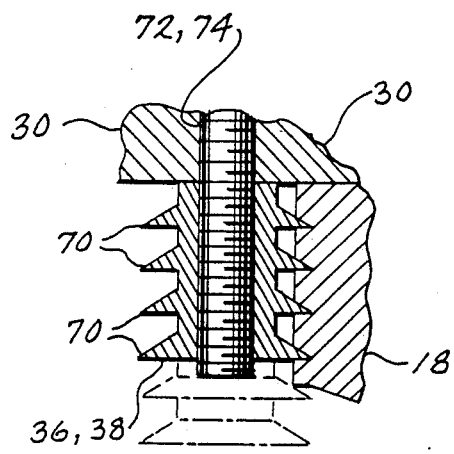
FIG. 7 is partial detail view showing a portion of the face plate assembly of FIG. 1.

As shown throughout the drawings, and as best seen FIG. 7, each of posts 36, 38 and 40 has a series of fins 70 along its length. Fins 70 extend about the circumference of each post at regularly spaced intervals, and have a sharp outer edge. As shown in FIG. 7, the sharp outer edge of the post engages a dental cast, such as shown at 18, to rigidly secure the cast to the body portion 30 when clamped between posts 36, 38 and 40. The sharp edges of fins 70 may become partially embedded in the dental cast to prevent movement of the cast after it has been mounted to body portion 30 of face plate assembly 12.

Fins 70 of posts 36, 38 and 40 allow selective positioning of dental cast 18 relative to upper frame member 4 in a direction toward and away from upper frame member 4.

With further reference to FIG. 7, it is seen that stationary posts 36, 38 are mounted on threaded studs 72, 74 extending through body portion 30 and projecting therefrom. Posts 36, 38 have an internal threaded passage adapted to mate with the projecting portion of studs 72, 74. Posts 36, 38 are movable in an up-down direction toward and away from body portion 30 of upper base plate assembly 12 by turning of posts 36, 38 about threaded studs 72, 74. This movability of stationary posts 36, 38 allows the base length of each post to be relatively short. As seen in FIG. 1, stationary posts 36, 38 engage the front portions of the dental casts adjacent the teeth portion; the short base length of posts 36, 38 provides minimal interference when working on the teeth portion of the dental casting. The movability of stationary posts 36, 38 toward and away from body portion 30 facilitates the adjustable positioning of dental cast 18 in such direction relative to upper frame member 4. Because movable post 40 engages the rear portion of the dental cast, it is longer than stationary posts 36, 38 and has a fixed height.

Figure 4:
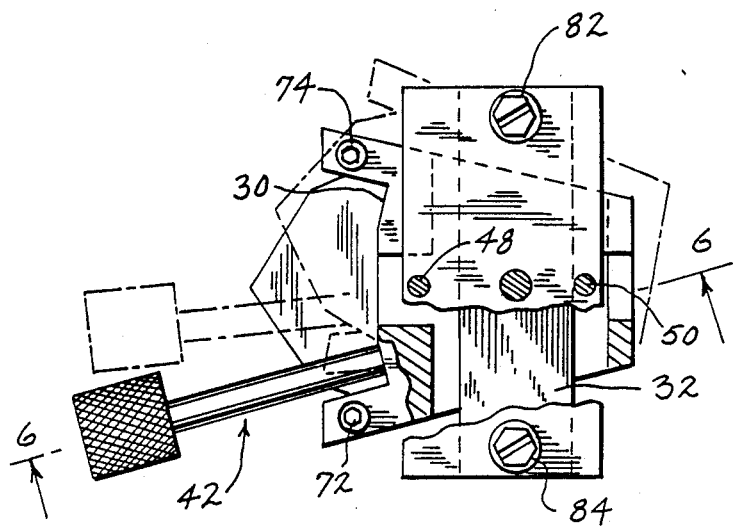
FIG. 4 is a top plan view, with portions broken away, showing the removable face plate assembly of FIG. 1.

Referring now to FIGS. 2–6, connector plate 32 is adapted to be received within a slot 76 provided in body portion 30 of upper face plate assembly 12. Slot 76 has a width substantially greater than that of connector plate 32, thus allowing lateral movement of connector plate 32 therein. Slot 76 is milled into body portion 30 so as to form a pair of upper lips 78, 80, which act to retain connector plate 32 within slot 76. With reference to FIG. 4, body portion 30 of upper face plate assembly 12 can be moved relative to connector plate 32 in both a left-right direction and in an up-down direction, due to the interaction of connector plate 32 with slot 76. This movement of body portion 30 is in a plane substantially parallel to a transverse plane generally extending through upper frame member 4 of articulator 2. The provision of such planar positioning of upper body portion 30, in combination with the up-down positioning provided by finned posts 36, 38 and 40, allows selective three-dimensional positioning of dental cast 18 relative to upper frame member 4.

Figure 5:
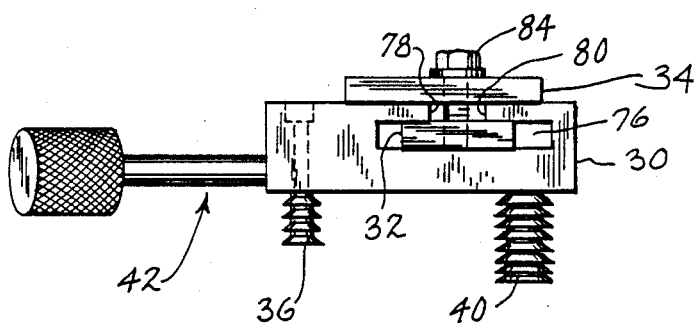
FIG. 5 is a side view of the face plate assembly of FIG. 1.

As a means for fixing the position of body portion 30 relative to connector plate 32, a pair of threaded clamping bolts 82, 84 (FIG. 4) extend through a pair of openings provided in the ends of clamping plate 34 and into threaded openings 86, 88 (FIG. 3) provided in the ends of connector plate 32. Thus, as seen in FIG. 5, when the appropriate lateral position of dental cast 18 mounted to body portion 30 is attained relative to upper frame member 4, clamping bolts 82, 84 are tightened down against the top of clamping plate 34 to draw connector plate 32 upwardly and thereby clamp lips 78 and 80 of body portion 30 between plates 32 and 34. This action fixes the position of body portion 30 relative to connector plate 32. In this manner, with dental cast 18 mounted to body portion 30, the position of the dental cast is thereby fixed relative to upper frame member 4 of articulator 2. Upon so fixing the position of the dental cast, face plate assembly can be removed from upper frame member 4 as a unit while articulator 2 is used for working on another set of dental casts. Thereafter, face plate assembly 12 can be reconnected to upper frame member 4, with locator holes 48, 50 and locator pins 44, 46 ensuring accurate positioning of upper face plate assembly 12 relative to upper frame member 4 of articulator 2. In this manner, a single articulator 2 can be used in connection with a series of base plate assemblies, such as 12, to allow a dentist or technician to work on numerous sets of dental casts, without requiring a dedicated articulator for each set being worked upon.

Figure 9:
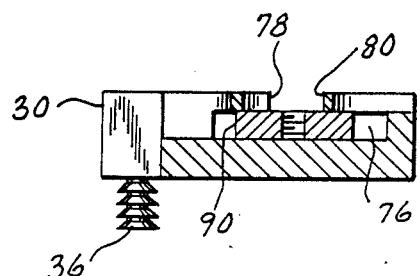
FIG. 9 is a sectional view taken generally along line 9—9 of FIG. 8.
Figure 8:
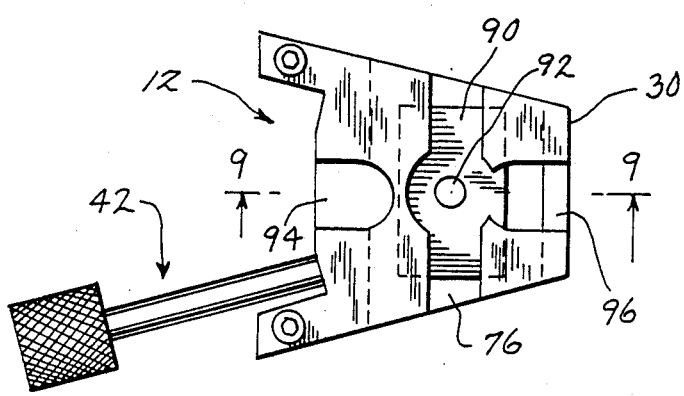
FIG. 8 is a top plan view of the face plate assembly of the present invention, incorporating an alternate mounting plate for connecting the face plate to a frame member of an articulator.

In a modified version of the invention, shown in FIGS. 8 and 9, connector plate 32 and clamping plate 34 are replaced with a shortened connector plate 90 in slot 76 of body portion 30. Connector plate 90 has a threaded opening 92 adapted to receive the threaded portion of mounting screw 14, for affixing upper face plate assembly 12 to upper frame member 4 of articulator 2. Milled slots 94 and 96 in the top of body portion 30 accommodate locator pins 44, 46 on the underside of upper frame member 4. With this arrangement, body portion 30 is movable relative to connector plate 90 via slot 76 to provide selective positioning of body portion 30 in a plane parallel to a transverse plane extending through upper frame member 4 of articulator 2. When the proper position of the dental cast mounted to body portion 30 is attained, mounting screw 14 is tightened down against the upper surface of upper frame member 4 to secure body portion 30 of upper base plate assembly 12 thereto. Once body portion 30 is so secured, it must remain in place on upper frame member until completion of the work being performed on the dental casts. This is because the position of body portion 30 is not fixed relative to connector plate 90 prior to connection of upper face plate assembly 12 to upper frame member 4. That is, after the upper face plate assembly 12 of FIG. 8 is removed from upper frame member 4, connector plate 90 will be free to move within slot 76 and the fixed position of the dental cast mounted to body portion 30 in a plane parallel to a transverse plane through upper frame member 4 will be lost. This version of the invention is suitable for a practitioner who infrequently uses an articulator, or who otherwise has no need for a face plate which is removable from the articulator with the dental cast mounted thereto.

The details of the present invention have been described with reference to upper face plate assembly 12. It is understood that lower face plate assembly 16 is of substantially the same construction as upper face plate assembly 12, and is likewise multidirectionally positionable to allow three-dimensional positioning of the dental cast mounted thereto relative to lower frame member 6 of articulator 2.

Various alternatives and modifications are contemplated as being within the scope of the following claims particularly pointing out and distinctly claiming the subject matter regarded as the invention.

I claim:

1. A removable face plate for providing removable plasterless mounting of a dental cast to a frame member of a dental articulator, said frame member including position fixing means, comprising:
   a body portion;
   plasterless mounting means provided on said body portion for mounting a dental cast thereto;
   lateral positioning means movably connected to said body portion, said lateral positioning means being removably engageable with the position fixing means provided on said articulator frame member, and providing lateral positioning of said body portion; and
   selectively actuable locking means for selectively securing said body portion and said positioning means together for preventing movement therebetween so that, upon engagement of said positioning means with the position fixing means provided on said articulator and actuation of said locking means, the position of said body portion relative to said articulator frame member is fixed.

2. The face plate of claim 1, wherein said plasterless mounting means comprises a plurality of mounting members connected to said face plate, said mounting members being adapted to engage said dental cast to rigidly secure said dental cast to said body portion.

3. The face plate of claim 2, wherein said mounting members comprise a plurality of mounting posts extending from said body portion of said face plate, and wherein one of said mounting posts is movable toward and away from another of said mounting posts to clamp said dental cast therebetween for securing said dental cast to said body portion.

4. The face plate of claim 3, wherein said mounting posts are provided with a plurality of fins formed along the length of said posts, said fins allowing said cast to be positioned in an up-down direction relative to said body portion and being adapted to engage the side portions of said dental cast after such positioning to secure said dental cast to said body portion of said face plate.

5. The face plate of claim 4, wherein one or more of said posts are attached to said body portion so that the amount of extension of said one or more posts from said body portion is adjustable to permit additional up-down positioning of said dental cast relative to said body portion.

6. The face plate of claim 1, wherein said lateral positioning means comprises a first member securable to said articulator frame member and engageable with the position fixing means provided thereon, and a second member interconnected with said body portion such that said body portion is laterally movable relative thereto, and wherein said selectively actuable locking means is operable so as to selectively secure said second member to said first member in a manner which prevents lateral movement of body portion relative to said first member so as to fix the lateral position of said body portion relative to said articulator frame member.

7. The face plate of claim 6, wherein said first member comprises a clamping plate securable to said articulator frame member, and wherein said second member comprises a connector plate disposed within a recess formed in said body portion for allowing lateral movement between said connector plate and said body portion.

8. The face plate of claim 7, wherein said position fixing means provided on said articulator frame member comprises one or more projections extending outwardly from said frame member, and wherein said clamping plate includes one or more mating recesses corresponding to and adapted to receive said one or more projections for fixing the position of said clamping plate relative to said articulator frame member when said clamping plate is secured thereto.

9. The face plate of claim 9, wherein said selectively actuable locking means comprises one or more threaded members extending between and engageable with said clamping plate and said connector plate, and wherein turning down said one or more threaded members draws said clamping plate and said connector plate together so as to clamp said body portion therebetween for fixing its position relative to said articulator frame member when said clamping plate is secured thereto.

10. The face plate of claim 9, wherein opposite end portions of said connector plate project outwardly from the recess in said body portion, and wherein said one or more threaded members comprise a threaded member connected to said connector plate adjacent its opposite end portions, with said body portion being movable on said connector plate between said threaded members.

11. The face plate of claim 6, wherein said plasterless mounting means includes means for providing up-down positioning of said cast relative to said articulator frame member after connection of said body portion thereto.

12. A dental articulator, comprising:
a pair of frame members, at least one of which is movable in a manner which replicates the operation of a human jaw;
locating means provided on at least a first one of said frame members; and
a removable face plate for providing removable plasterless mounting of a dental cast to said first frame member, comprising:
a body portion;
plasterless mounting means provided on said body portion for mounting a dental cast thereto;
lateral positioning mans movably connected to said body portion, said lateral positioning means including a portion removably securable to said first frame member having means for engaging said locating means provided on said first frame member, for fixing the position of the portion of said positioning means relative to said frame member when secured thereto, said positioning means providing lateral positioning of said body portion; and
selectively actuable locking means for selectively securing said body portion and said positioning means together for preventing movement therebetween so that, upon engagement of said positioning means with said floating means provided on said articulator frame member and actuation of said locking means, the position of said body portion relative to said articulator frame member is fixed.

* * * * *

UNITED STATES PATENT AND TRADEMARK OFFICE
CERTIFICATE OF CORRECTION

PATENT NO. : 4,923,398

DATED : 5/8/90

INVENTOR(S) : Jay L. Mackman

It is certified that error appears in the above-identified patent and that said Letters Patent is hereby corrected as shown below:

Claim 9, Col. 7, Line 39, Change dependency from "9" to --- 7 ---;

Claim 12, Col. 8, Line 26, Delete "mans" and substitute therefor --- means ---;

Claim 12, Col. 8, Line 40, Delete "floating" and substitute therefor --- locating ---.

Signed and Sealed this

Ninth Day of July, 1991

Attest:

HARRY F. MANBECK, JR.

*Attesting Officer*     Commissioner of Patents and Trademarks